United States Patent
Schöndube et al.

(10) Patent No.: US 11,975,319 B2
(45) Date of Patent: May 7, 2024

(54) DISPENSING DEVICE HAVING A DISPENSER FOR DISPENSING A LIQUID CONTAINING AT LEAST ONE CELL AND/OR AT LEAST ONE PARTICLE

(71) Applicant: cytena GmbH, Freiburg (DE)

(72) Inventors: Jonas Schöndube, Freiburg (DE); Lena Lautscham, Freiburg (DE)

(73) Assignee: CYTENA GMBH, Freiburg (DE)

( * ) Notice: Subject to any disclaimer, the term of this patent is extended or adjusted under 35 U.S.C. 154(b) by 849 days.

(21) Appl. No.: 17/049,608

(22) PCT Filed: Apr. 23, 2019

(86) PCT No.: PCT/EP2019/025118
§ 371 (c)(1),
(2) Date: Oct. 22, 2020

(87) PCT Pub. No.: WO2019/206459
PCT Pub. Date: Oct. 31, 2019

(65) Prior Publication Data
US 2021/0237049 A1    Aug. 5, 2021

(30) Foreign Application Priority Data

Apr. 23, 2018  (LU) ........................................ 100778

(51) Int. Cl.
| B01L 3/02 | (2006.01) |
| C12M 1/00 | (2006.01) |
| G01N 15/00 | (2006.01) |
| G01N 15/14 | (2006.01) |

(52) U.S. Cl.
CPC ........... B01L 3/0293 (2013.01); C12M 47/04 (2013.01); G01N 15/1456 (2013.01);
(Continued)

(58) Field of Classification Search
None
See application file for complete search history.

(56) References Cited

U.S. PATENT DOCUMENTS

| 4,609,286 A | 9/1986 | Sage, Jr. |
| 4,662,742 A | 5/1987 | Chupp |

(Continued)

FOREIGN PATENT DOCUMENTS

| JP | 2010286565 A | 12/2010 |
| WO | 2017220509 A1 | 12/2017 |

OTHER PUBLICATIONS

Davidson College, Fluorescence Activated Cell Sorting (FACS), <https://www.bio.davidson.edu/courses/genomics/method/facs.html>, cached by Internet Archive Mar. 10, 2016, accessed Sep. 19, 2023 (Year: 2016).*

(Continued)

Primary Examiner — Holly Kipouros
(74) Attorney, Agent, or Firm — Hodgson Russ LLP

(57) ABSTRACT

The invention relates to a dispensing device having a dispenser for dispensing a liquid containing at least one cell and/or at least one particle and an optical detection device for optically detecting at least a region of the dispenser, which has a light source for emitting an illuminating light for illuminating the region and a deflection device for deflecting a detection light emanating from the region. The dispensing device is characterised in that the deflection device deflects the detection light at least twice, in particular exactly twice.

21 Claims, 2 Drawing Sheets

(52) U.S. Cl.
CPC . *B01L 2200/0652* (2013.01); *B01L 2200/143* (2013.01); *B01L 2300/0663* (2013.01); *B01L 2300/168* (2013.01); *G01N 2015/0053* (2013.01); *G01N 2015/1486* (2013.01)

(56) References Cited

U.S. PATENT DOCUMENTS

| | | | | |
|---|---|---|---|---|
| 2006/0023207 | A1* | 2/2006 | Cox | G01N 15/1404 356/338 |
| 2007/0070347 | A1* | 3/2007 | Scherer | G01N 21/05 356/454 |
| 2014/0246624 | A1* | 9/2014 | Seubert | B82Y 15/00 423/566.1 |
| 2017/0315039 | A1 | 11/2017 | Beil et al. | |

OTHER PUBLICATIONS

Labome, Flow Cytometry—A Survey and the Basics, <https://www.labome.com/method/Flow-Cytometry-A-Survey-and-the-Basics.html>, cached by the Internet Archive May 18, 2016, accessed Sep. 21, 2023 (Year: 2016).*

Riba J et al, "Label-free isolation and deposition of single bacterial cells from heterogeneous samples for clonal culturing", Scientific Reports, Sep. 6, 2016, vol. 6, No. 1, pp. 1-9.

Shin D-Y et al, "Rapid jetting status inspection and accurate droplet volume measurement for a piezo drop-on-demand inkjet print head using a scanning mirror for display applications", Review of Scientific Instruments, Feb. 13, 2017, vol. 88, No. 2, pp. 025109-1-025109-13.

Ortega Arroyo J et al, "Label-Free, All-Optical Detection, Imaging, and Tracking of a Single Protein", Nano Letters, Apr. 9, 2014, vol. 14, No. 4, pp. 2065-2070.

Drechsler A et al, "Confocal microscopy with a high numerical aperture parabolic mirror", Optics Express, Dec. 3, 2001, vol. 9, No. 12, pp. 637-644.

Gross A et al, "Single-Cell Printer: Automated, On Demand, and Label Free", Journal of Laboratory Automation, Dec. 1, 2013, vol. 18, pp. 504-518, URL:http://jla.sagepub.com/content/18/6/504.full.pdf.

CNIPA, First Office Action for CN Application No. 201980027610.1, dated Jun. 30, 2023.

* cited by examiner

DISPENSING DEVICE HAVING A DISPENSER FOR DISPENSING A LIQUID CONTAINING AT LEAST ONE CELL AND/OR AT LEAST ONE PARTICLE

CROSS-REFERENCE TO RELATED APPLICATIONS

The present application is the U.S. national phase of International Application No. PCT/EP2019/025118 filed Apr. 23, 2019, which claims the benefit of and priority to Luxembourgian Patent Application No. 100778 filed Apr. 23, 2018, the entire disclosure of which is incorporated herein by reference.

FIELD

The disclosure relates to a dispensing device having a dispenser for dispensing a liquid containing at least one cell and/or at least one particle and an optical detection device for optically detecting at least a region of the dispenser, which has a light source for emitting an illuminating light for illuminating the region and a deflection device for deflecting a detection light emanating from the region.

BACKGROUND

It is known from the prior art that active substances, such as monoclonal antibodies and other proteins, are produced with the aid of so-called monoclonal cell lines. These are populations of cells that are all descended from a single parent cell. The production of monoclonal cell lines is necessary because this is the only way to ensure that all cells of the population have approximately the same genome in order to produce active ingredients of a constant and reproducible quality.

In order to produce a monoclonal cell line, cells are transferred individually into the containers of a microtitre plate. The cells to be transferred are produced by genetically modifying a host cell line and isolating these modified cells. Individual cells are deposited in the microtitre plates by a dispensing device. After the cells have been deposited in the respective containers of the microtitre plate, the cells can grow and may then be transferred to a bioreactor.

The user of the dispensing device wants to know whether each liquid deposited in the container of the microtitre plate contains a cell and/or a particle. The dispensing device therefore usually has an optical detection device which is used to determine whether the dispensed liquid contains a cell and/or a particle.

In order to obtain images with a high resolution, it is recommended that the optical detection device be placed as close as possible to a dispenser of the dispensing device. However, this is not possible due to the structural conditions. The distance between the dispenser and the container for receiving the dispensed liquid should be as small as possible so that it is ensured that the dispensed liquid actually ends up in the container. However, this means that the optical detection apparatus cannot be arranged close to the dispenser and thus complex optical detection apparatus have to be used.

RIBA J ET AL: "Label-free isolation and deposition of single bacterial cells from heterogeneous samples for clonal culturing", SCIENTIFIC REPORTS, vol. 6, No. 1, Sep. 6, 2016, discloses a device for dispensing a liquid which may contain bacterial cells. The device has an optical detection device having an objective and a deflection mirror.

SHIN D-Y ET AL: "Rapid jetting status inspection and accurate droplet volume measurement for a piezo drop-on-demand inkjet print head using a scanning mirror for display applications", REVIEW OF SCIENTIFIC INSTRUMENTS, AIP, MELVILLE, NY, US, Vol. 88, No. 2, Feb. 13, 2017, discloses an ink jet printhead having a rotatable mirror.

ORTEGA ARROYO J ET AL: "Label-Free, All-Optical Detection, Imaging, and Tracking of a Single Protein", NANO LETTERS, Vol. 14, No. 4, Apr. 9, 2014 discloses a device for detecting, receiving and tracking a single protein. The device has a polarising beam splitter which deflects detection light to a CMOS camera.

DRECHSLER A ET AL: "Confocal microscopy with a high numerical aperture parabolic mirror", OPTICS EXPRESS, Vol. 9, No. 12, Dec. 3, 2001 discloses a confocal microscope having a parabolic mirror.

Gross A ET AL: "Single-Cell Printer: Automated, On Demand, and Label Free", Journal of Laboratory Automation Society for Laboratory Automation and Screening, Vol. 18, Dec. 1, 2013 discloses a device for dispensing a liquid. The device has a receiving device for receiving the dispensed liquid.

WO 2017/220 509 A1 discloses a device for detecting cells or particles in a fluid container. The device comprises a dispenser which is used to dispense at least one cell or at least one particle. In addition, the device has a detection apparatus for detecting the cell or the particle.

SUMMARY

An object of the disclosure is therefore to provide an improved dispensing device.

The object is achieved by a dispensing device of the type mentioned at the outset, which is characterised in that the deflection device deflects the detection light at least twice, in particular exactly twice.

The device according to the disclosure has the advantage that a high resolution and/or a high magnification of the region under consideration can be achieved even when using a standard objective. This is possible because a higher numerical aperture can be used due to the deflection device. In particular, it is not necessary to use expensive objectives in the device according to the disclosure, but a more cost-effective standard objective can be used. The provision of the deflection device also offers the advantage that the components of the optical detection device, described in more detail below, do not have to be moved for optically detecting the region of the dispenser, in particular do not have to be moved relative to the dispenser.

Another advantage of the disclosure is that a region of the dispenser is illuminated with the illuminating light. Thus, by looking at the region of the dispenser, it can be determined whether the liquid to be dispensed contains a cell or a particle. The region of the dispenser preferably corresponds to an output area of the dispenser, in particular an output area of the dispenser having a nozzle. It is therefore not necessary to look at the liquid that is actually dispensed from the dispenser. Viewing the region of the dispenser offers the advantage that no optical elements have to be arranged between the dispenser and a microtitre plate. Therefore, the distance between the dispenser and the microtitre plate can be small.

The liquid, in particular a drop of liquid, is dispensed by means of the dispenser. The dispensed liquid might contain no cells and/or particles. Alternatively, the dispensed liquid might contain exactly one single cell or multiple cells and/or one single particle or multiple particles.

The dispenser can be fluidically connected to a liquid reservoir of the dispensing device. The drop of liquid can thereby have at least one cell and/or at least one particle. The dispensed liquid has a volume in a range between 10 pl (picolitres) to 50 nl (nanolitres). The fluid can be a cell suspension that promotes cell growth. The particle can be a glass or polymer bead and have substantially the same volume as the cell. The light source can be an LED lamp.

The detection light emanating from the region as a result of the illumination of the region with the illuminating light can be detected. The detected detection light can be read out by means of a read-out device described in more detail below and then evaluated.

In a particular embodiment, the deflection device can deflect the illuminating light at least twice, in particular exactly twice. This means that the deflection device is designed and arranged in such a way that it deflects both the detection light and the illuminating light. As a result, a compact optical detection device can be realised. In this case, the detection light can be deflected substantially by 90°, in particular precisely by 90°, during each deflection process. Similarly, the illuminating light can be deflected substantially by 90°, in particular precisely by 90° in each case, during each deflection process.

In addition, the deflection device can be designed in such a way that the illuminating light exiting through a first side of the deflection device is deflected at least twice to the illuminating light entering through a second side. The deflection device can be designed in such a way that the illuminating light exiting from the deflection device runs offset from the illuminating light entering the deflection device. In particular, the deflection device can displace the illuminating light exiting from the deflection device substantially parallel, in particular parallel, to the illuminating light entering the deflection device. The deflection of the illuminating light can take place analogously to the detection light in each deflection process substantially by 90°, in particular precisely by 90°.

The detection light exiting from the deflection device can run offset to the detection light entering the deflection device. It is particularly advantageous if the detection light exiting from the deflection device is displaced substantially parallel, in particular parallel, to the detection light entering the deflection device. In addition, the deflection device can be designed in such a way that the detection light exiting through the second side of the deflection device is deflected at least twice to the detection light entering through the first side.

In a special embodiment, the deflection device can have at least one prism for deflecting the illuminating light and/or the detection light. The prism offers the advantage that the illuminating light exiting from the prism can be offset in a simple manner, in particular displaced parallel, to the illuminating light entering the prism. Equally, the detection light exiting from the prism can easily be offset, in particular displaced parallel, with respect to the detection light entering the prism. The displacement takes place particularly easily if the prism has a base area with at least four, in particular exactly four, corners. The prism can be an oblique prism, in particular a parallelepiped. The prism can preferably be a rhombohedron. The use of a prism has the advantage that an exact parallel displacement of the illuminating light and/or the detection light can be realised.

When using the prism, the first side corresponds to a lateral surface of the prism and the second side corresponds to another lateral surface of the prism. The first side, in particular the lateral surface, and the second side, in particular the other lateral surface, can run parallel to one another.

Alternatively or additionally, the deflection device can have at least two mirrors for deflecting the illuminating light and/or the detection light. Regardless of whether the deflection device has the prism or the mirror, the deflection device is designed in both cases in such a way that it deflects the illuminating light in the direction of the region of the dispenser so that the region of the dispenser is illuminated by the illuminating light.

The optical detection device can have an objective. The objective is a collecting optical system that creates a real optical image of the object. The deflection device can be arranged in the beam path of the illuminating light and/or detection light between the objective and the dispenser. This enables the deflection device to be mechanically connected to the dispenser, whereby a compact device can be realised. In particular, the deflection device can be attached to the dispenser, in particular directly. This enables the distance between the objective and the dispenser to be small, which in turn is advantageous for the resolution and the magnification.

The deflection device can deflect the illuminating light directly into the region of the dispenser. This means that no further optical elements are arranged between the dispenser and the deflection device in the beam path of the illuminating light. In addition, the deflection device can deflect the detection light directly into the objective. This means that no further optical elements are arranged between the objective and the deflection device in the beam path of the detection light.

At least one lens can be attached or arranged on the side of the deflection device facing the dispenser, in particular the prism. The lens can have a planar side which is attached to the side of the deflection device facing the dispenser, in particular the light exit side. The planar side of the lens can be attached, preferably directly, to a lateral surface of the prism. By using the lens, imaging errors that result in particular from a spherical aberration can be at least partially eliminated in a simple manner.

The objective can be arranged in such a way that an optical axis of the objective runs transversely, in particular perpendicular, to an output direction of the liquid from the dispenser. Such an arrangement of the objective offers the advantage that the objective can be arranged closer to the dispenser than with the known dispensing devices, in which the objective is arranged above the dispenser. As a result, the above-described arrangement of the objective increases the resolution and/or the magnification.

The dispensing device can have an actuator for actuating the dispenser. The actuator can be a piezo actuator. The objective and the actuator can be opposite each other in relation to the dispenser. In particular, the actuator and the objective can lie opposite one another in relation to a plane which runs in the same direction as a direction of discharge of the liquid from the dispenser.

In a particular embodiment, the optical detection device can have a read-out device for reading out the detected detection light emanating from the region of the dispenser. The read-out device is used for reading out the information contained in the detected detection light. The detection light results from illuminating the region with the illuminating light and/or has, for example, illuminating light reflected on the cells and/or particles.

The detection light and the illuminating light can at least partially have a common beam path. The common beam path can have at least the objective and the deflection device.

In addition, the optical detection device can have an imaging device. Based on the detected detection light, the imaging device can generate an image. In particular, an image of the region of the dispenser can be generated by means of the imaging device. The region of the dispenser can have the output area of the dispenser, in particular the nozzle of the dispenser. The read-out device can be integrated in the imaging device. The imaging device can be a camera.

The optical detection device can also have an evaluation device for evaluating the detected detection light. The evaluation device can evaluate the detected detection light in order to determine an optical property of the region. In particular, the evaluation device can evaluate the information read out by means of the read-out device. For example, a transparency and/or a contrast and/or degree of reflection of the region can be determined as an optical property. Alternatively or additionally, further optical properties of the region can also be determined.

Based on the detected detection light, in particular based on the certain optical property of the region, the evaluation device can determine whether no cell and/or no particle is arranged in the region of the dispenser or whether a single cell and/or a single particle is arranged in the region of the dispenser is arranged or several cells and/or several particles are arranged. As a result, the number of cells and/or particles arranged in the region can be determined in a simple manner by the evaluation device. The evaluation device can be integrated in the imaging device.

An algorithm for at least partial elimination of an imaging error that results, for example, from the spherical aberration, can be stored in the evaluation device. As a result, images with a better quality can be generated by the imaging device.

In a particular embodiment, the optical detection device can have a further light source for dispensing an excitation light for illuminating the at least one region of the dispenser and/or at least one other region of the dispenser. The further light source can be a laser. A very particular embodiment is obtained when the excitation light and the illuminating light at least partially have a common beam path. In this embodiment, a simple and compact optical detection system is obtained. The common beam path can have at least the objective and the deflection device.

The read-out device can be arranged and designed in such a way that it reads out a detected further detection light emanating from the region of the dispenser. The further detection light results from the illumination of the region and/or the other region of the dispenser. The further detection light can be deflected twice by the deflection device, analogously to the detection light. In particular, the further detection light exiting from the deflection device can be displaced substantially parallel, in particular parallel, to the further detection light entering the deflection device.

Based on the detected further detection light, the imaging device can generate a further image of the region and/or the other region. In addition, the evaluation device can evaluate the further detection light to determine a further optical property of the region and/or the other region. The further optical property can be fluorescence of the cell arranged in the region and/or of the particle arranged in the region. In this case, the excitation light is used for exciting the cell and/or the particle. The excitation light is absorbed by a fluorescent substance of the cell and/or a fluorescent substance of the particle. The further detection light emitted by the cell and/or the particle corresponds to a fluorescent light. Based on the further detection light, the evaluation device can determine whether no fluorescent cell and/or no fluorescent particle is arranged in the region and/or other region or whether exactly one single fluorescent cell and/or exactly one single fluorescent particle is arranged in the region and/or other region and/or whether several cells and/or several particles are arranged in the region.

The further detection light and the excitation light can at least partially have a common beam path. The common beam path can have at least the objective and the deflection device.

The use of the read-out device for reading out the detected detection light and the detected further detection light and the imaging device for generating the image and the further image and the evaluation device for determining the further optical property offers the advantage that an optical detection system is implemented with few elements.

The provision of the deflection device is particularly advantageous in the embodiment in which it is determined whether a fluorescent cell and/or a fluorescent particle is arranged in the region. As already described above, the provision of the deflection device offers the advantage of a higher numerical aperture. This means that, due to the resulting larger emission angle, a larger area is covered in which the photons emanating from the cell and/or the particle can reach the objective. In this respect, a better image of the region can also be obtained due to the deflection device. In addition, due to the larger radiation angle, the cell and/or the particle can be excited for a shorter period of time, which enables the liquid to be dispensed from the dispenser more quickly.

In an alternative embodiment, the optical detection device can have a further read-out device for reading out a detected further detection light. In addition, the optical detection device can have a further imaging device for generating a further image of the region and/or the other region based on the detected further detection light and/or a further evaluation device. The further evaluation device can evaluate the further detection light to determine the further optical property of the region. Based on the further detection light, the further evaluation device can determine whether no fluorescent cell and/or no fluorescent particle is arranged in the region and/or other region or whether exactly one single fluorescent cell and/or exactly one single fluorescent cell is arranged in the region and/or other region fluorescent particle is arranged and/or whether several cells and/or several particles are arranged in the region. The further imaging device can be a camera and/or the further evaluation device and/or the further read-out device can be integrated in the imaging device.

The dispensing device can have a deflection and/or suction device. The diversion device is used for diverting the dispensed liquid, in particular the dispensed liquid drop. The suction device is used for siphoning off the dispensed liquid. The dispensed liquid can be diverted and/or siphoned off into a reject container. The deflection and/or suction can take place before the dispensed liquid enters the container, in particular the container of a microtitre plate. The dispensed liquid can be deflected and/or siphoned off if the liquid contains no cells and/or no particles. Alternatively, the dispensed liquid can be deflected and/or siphoned off if the number of cells and/or particles contained in the liquid is greater than a predefined value, in particular greater than 1.

BRIEF DESCRIPTION OF THE DRAWING VIEWS

The subject of the disclosure is shown schematically in the figures, wherein elements that are the same or have the same effect are mostly provided with the same reference symbols. In the figures.

DETAILED DESCRIPTION

Figure 1:
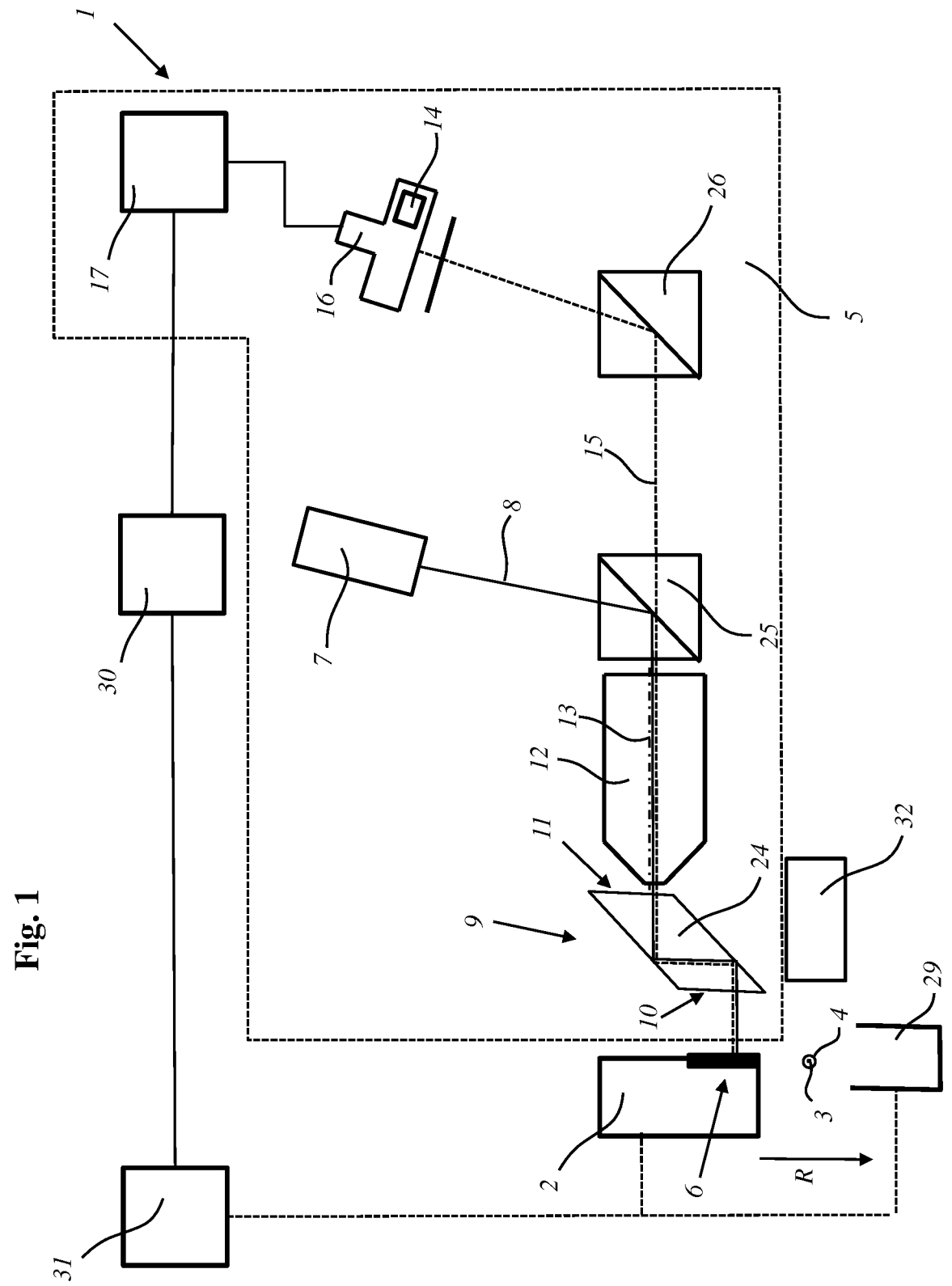
FIG. 1 shows a schematic representation of a dispensing device according to the disclosure according to a first embodiment.

FIG. 1 shows a dispensing device 1 which has a dispenser 2 for dispensing a liquid 4 containing at least one cell 3 and/or at least one particle and an optical detection device 5 for optically detecting at least one region 6 of the dispenser 2. The optical detection device 5 has a light source 7, such as an LED lamp, for emitting an illuminating light 8 and a deflection device 9 having a prism 24. The illuminating light 8 is used for illuminating the region 6 and is deflected twice by the deflection device 9. A detection light 15 then emanating from region 6 is also deflected twice by the deflection device 9.

The deflection device 9 is designed in such a way that the illuminating light 8 exiting through the first side 10 of the prism is displaced parallel to the illuminating light 8 entering through the second side 11 of the prism. Likewise, the detection light 15 exiting through the second side 11 of the prism is displaced parallel to the detection light 15 entering through the first side 10 of the prism. FIG. 1 shows a state in which the light source 7 emits the illuminating light 8.

The deflection device 9 is arranged in such a way that it deflects the illuminating light 8 to the region 6 of the dispenser 2. The region 6 of the dispenser 2 corresponds to an output area of the dispenser 2. FIG. 1 shows a state in which the dispenser 2 has dispensed a liquid 4, in particular a drop of liquid, which contains a cell 3. The liquid 4 is fed into a container 29. The dispenser 2 is actuated by an actuator, not shown, in particular a piezo actuator.

The optical detection device 5 also has an objective 12. The objective 12 is arranged in such a way that an optical axis 13 of the objective 12 runs perpendicular to an output direction R of the liquid 4 from the dispenser 2. The deflection device 9 is arranged in the beam path of the illuminating light 8 and/or of the detection light 15 between the dispenser 2 and the objective 12.

In addition, the optical detection device 5 has a filter 25 which is arranged in the beam path of the illuminating light 8 between the objective 12 and the light source 7. The filter 25 is designed in such a way that it deflects the illuminating light 8 in the direction of the objective 12. In addition, the filter 25 is designed in such a way that it lets through the detection light 15 emanating from the region 6, which is shown in dashed lines in FIG. 1. The detection light 15 let through by the filter 25 is deflected by a beam deflector 26 in the direction of an imaging device 16. The detection light 15 and the illuminating light 8 partially have a common beam path.

A read-out device 14 arranged in the imaging device 16 reads out the detection light 15 detected by a detector of the imaging device 16. Based on the detected detection light 15, in particular on the information read out by the read-out device 14, the imaging device 16 can generate an image of the region 6.

The imaging device 16 is electrically connected to an evaluation device 17, which is for example a computer, of the optical detection device 5. The evaluation device 17 can evaluate the recorded detection light 15. In particular, the evaluation device 17 can evaluate the information read out by means of the read-out device 14. Based on the detection light 15, the evaluation device 17 can determine an optical property of the region 6. By determining the optical property of region 6, it is possible to determine whether no cell 3 and/or no particle is arranged in the illuminated region or at least one cell 3 and/or at least one particle is arranged The evaluation device 17 is electrically connected to a control device 28. Based on the evaluation result of the evaluation device 17, the control device 30 controls the dispensing process of the dispenser 2. The control device 30 is electrically connected to a moving device 29. The moving device 29 can move the dispenser 2 and/or the container 29 in such a way that the liquid 4 can be dispensed into the desired storage location.

In addition, the control device 30 can control a deflection and/or suction device 32 of the dispensing device 1. The control device 30 can control the deflection and/or suction device 32 in such a way that the dispensed liquid 4 is deflected and/or siphoned off if no cell 3 and/or no particle is arranged in the liquid 4 or if several cells 3 and/or several particles are arranged in the liquid 4.

Figure 2:
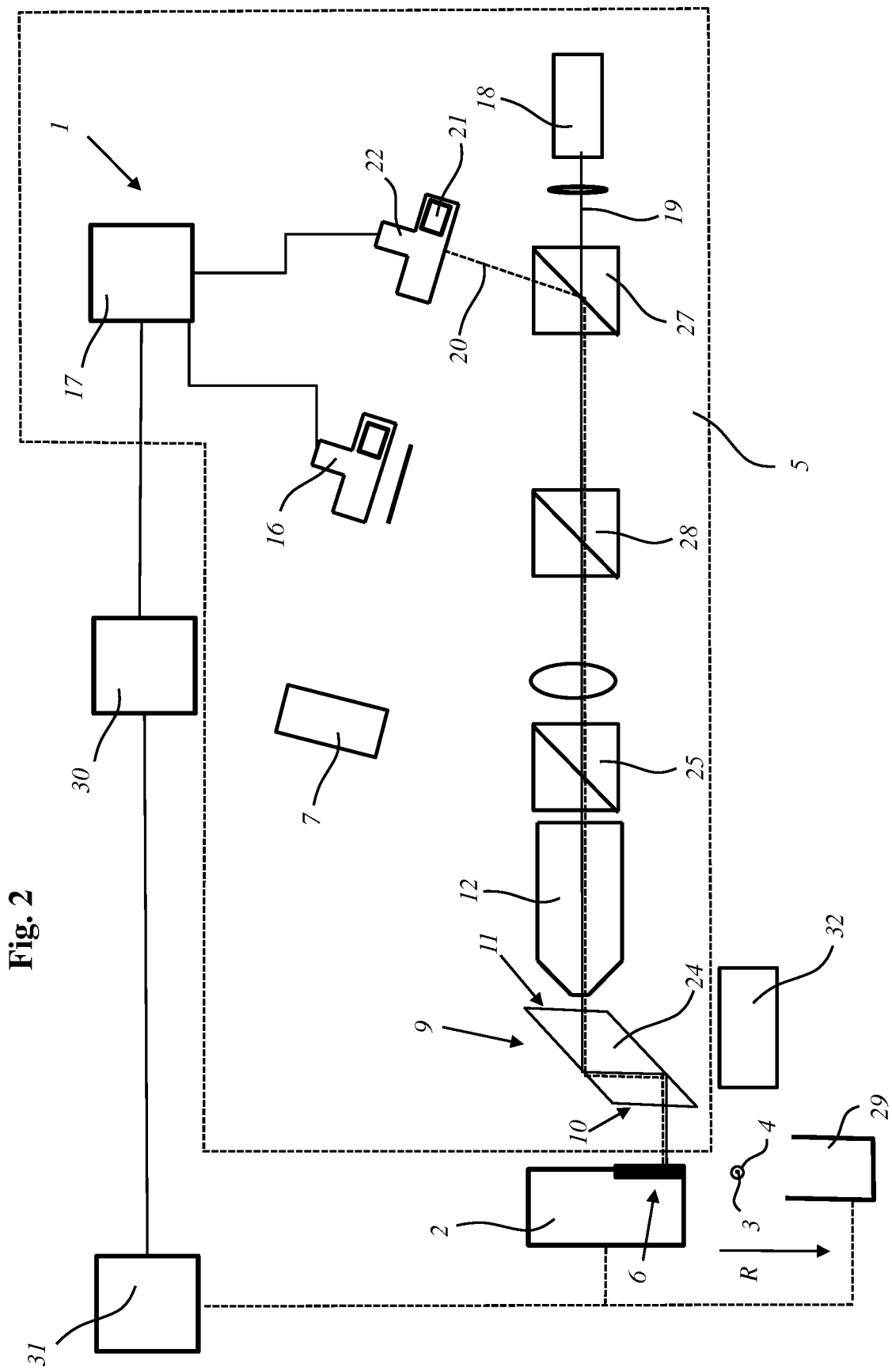
FIG. 2 shows a schematic representation of a dispensing device according to the disclosure according to a second embodiment.

FIG. 2 shows a schematic representation of a dispensing device according to the disclosure according to a second embodiment. The second embodiment differs from the first embodiment shown in FIG. 1 in that the optical detection device 5 additionally has a further light source 18, a further imaging device 22 and a further read-out device 21. The further light source 18 can be a laser and the further imaging device 22 can be a camera. FIG. 2 shows a state in which the further light source 18 emits an excitation light 19. In contrast, the light source 7 does not emit any illuminating light 8.

Another difference is that the second embodiment has a further filter 28 instead of the beam deflector 26. The further filter 28 is designed in such a way that it deflects the detection light 15, not shown, to the imaging device 16. In addition, the further filter 28 is designed in such a way that it lets through a further detection light 20. The optical detection device 5 also has a further beam deflector 27 which deflects the further detection light 20 in the direction of the further imaging device 22, wherein the further detection light 20 is detected by a detector of the further imaging device 22. The further detection light 20 is deflected twice by the deflection device 9, analogously to the detection light 15.

The further light source 18 emits the excitation light 19 for illuminating the region 6 of the dispenser 2, which is passed through the further beam deflector 27, the further filter 28, the filter 25 to the objective 12. The excitation light 19 and the illuminating light 8 have a common beam path. In particular, both the illuminating light 8 and the excitation light 19 are passed through the objective 12 and the deflection device 9.

The detected further detection light 20 emanating from the region 6 as a result of the excitation light 19 is read out by the further read-out device 21. The further detection light 20 can be fluorescent light emitted by the cell 3 and/or by the particle, provided that a cell 3 and/or a particle with fluorescent properties is arranged in the region 6 of the dispenser 2. Based on the further detection light 20, the further imaging device 22 can generate a further image of the region 6 of the dispenser 2. The further evaluation device 23 evaluates the further detection light 20 and determines whether no fluorescent cell 3 and/or no fluorescent particle is arranged in region 6 or whether at least one cell 3 and/or at least one particle is arranged in the region 6.

The excitation light 19 and the further detection light 20 partially have a common beam path.

LIST OF REFERENCE NUMBERS

1 Dispensing device
2 Dispenser
3 Cell
4 Liquid
5 Optical detection device
6 Region
7 Light source
8 Illuminating light
9 Deflection device
10 First side
11 Second side
12 Objective
13 Optical axis
14 Read-out device
15 Detection light
16 Imaging device
17 Evaluation device
18 Further light source
19 Excitation light
20 Further detection light
21 Further read-out device
22 Further imaging device
23 Further evaluation device
24 Prism
25 Filter
26 Beam deflector
27 Further beam deflector
28 Further filter
29 Container
30 Control device
31 Moving device
32 Deflection and/or suction device
R Output direction

What is claimed is:

1. A dispensing device (1) comprising: a dispenser (2) for dispensing a liquid (4) containing at least one cell (3) and/or at least one particle, an objective lens (12) having an optical axis (13), and an optical detection device (5) for optically detecting at least a region (6) of the dispenser (2), the optical detection device (5) having a light source (7) for emitting an illuminating light (8) for illuminating the region (6) and a deflection device (9) arranged between the dispenser (2) and the objective (12) for deflecting a detection light (15) emanating from the region (6), wherein the deflection device (9) deflects the detection light (15) at least twice to direct the detection light (15) from the region (6) of the dispenser (2) to the objective (12).

2. The dispensing device (1) according to claim 1, wherein the illuminating light (8) enters the deflection device (9) through a second side (11) of the deflection device (9) and exits the deflection device (9) through a first side (10) of the deflection device (9) as the illuminating light (8) travels to the region (6), and wherein
   a. the deflection device (9) deflects the illuminating light (8) at least twice, and/or
   b. the illuminating light (8) exiting through the first side (10) of the deflection device is deflected at least twice by the deflection device (9) relative to the illuminating light (8) entering through the second side (11) of the deflection device and/or
   c. the illuminating light (8) exiting from the deflection device (9) runs offset to the illuminating light (8) entering the deflection device (9) and/or
   d. the illuminating light (8) exiting from the deflection device (9) is displaced substantially parallel to the illuminating light (8) entering the deflection device.

3. The dispensing device according to claim 1, wherein
   a. the detection light (15) exiting from the deflection device (9) runs offset to the detection light (15) entering the deflection device (9) and/or
   b. the detection light (15) exiting from the deflection device (9) is displaced substantially parallel to the detection light (15) entering the deflection device (9) and/or
   c. the detection light (15) exiting through a second side (11) of the deflection device (9) is deflected at least twice by the deflection device (9) relative to the detection light (15) entering through a first side (10) of the deflection device.

4. The dispensing device (1) according to claim 1, wherein
   a. the deflection device (9) has at least one prism (24) for deflecting the detection light (15) and/or the illuminating light (8) and/or
   b. the deflection device (9) has at least one prism (24) with a base area which has at least four corners and/or
   c. the deflection device (9) has at least one oblique prism and/or
   d. the deflection device (9) has a prism (24), wherein a first side (10) of the prism (24) through which illuminating light (8) exits from the prism (24) runs parallel to a second side (11) of the prism (24) through which illuminating light (8) enters the prism (24).

5. The dispensing device (1) according to claim 1, wherein the deflection device (9) has at least two mirrors for deflecting the detection light (15) and/or the illuminating light (8).

6. The dispensing device (1) according to claim 1, wherein
   the deflection device (9) is arranged in the beam path of the illuminating light (8) between the objective (12) and the dispenser (2).

7. The dispensing device (1) according to claim 6, wherein the objective (12) is arranged such that the optical axis (13) of the objective (12) runs transversely to an output direction (R) of the liquid from the dispenser (2).

8. The dispensing device (1) according to claim 1, wherein
   a. the deflection device (9) is mechanically connected to the dispenser (2) and/or
   b. the deflection device (9) is attached to the dispenser (2) and/or
   c. the deflection device (9) deflects the illuminating light (8) directly into the region (6); and/or
   d. a lens is attached to a side of the deflection device (9) facing the dispenser (2) or
   e. a lens having a planar side is attached to a side of the deflection device (9) facing the dispenser (2).

9. The dispensing device (1) according to claim 1, further comprising an actuator for actuating the dispenser (2), wherein
 a. the actuator is a piezo actuator and/or
 b. the actuator and the objective (12) are opposite each other in relation to the dispenser (2).

10. The dispensing device (1) according to claim 1, wherein the optical detection device (5) detects the detection light (15) emanating from the region (6) of the dispenser (2).

11. The dispensing device (1) according to claim 10, wherein the optical detection device (5) has an imaging device (16), wherein
 a. based on the detected detection light (15), the imaging device (16) generates an image and/or
 b. the imaging device (16) generates an image of the region (6) of the dispenser (2).

12. The dispensing device (1) according to claim 11, wherein
 a. the optical detection device (5) has an evaluation device (17) for evaluating the detected detection light (15), or
 b. the optical detection device (5) has an evaluation device (17) for evaluating the detected detection light (15), wherein an algorithm for at least partial elimination of an imaging error is stored in the evaluation device (17).

13. The dispensing device (1) according to claim 12, wherein
 a. the evaluation device (17) evaluates the detected detection light (15) to determine an optical property of the region (6) of the dispenser (2) or
 b. based on the detected detection light (15), the evaluation device (17) determines whether no cell (1) and/or no particle is arranged in the region (6) of the dispenser (2) or whether exactly one single cell (3) and/or one single particle is arranged in the region (6) of the dispenser (2) or whether several cells and/or several particles are arranged in the region (6) of the dispenser (2).

14. The dispensing device (1) according to claim 13, wherein the optical detection device (5) has a further light source (18) for dispensing an excitation light (19) for illuminating the at least one region (6) of the dispenser (2) and/or at least one other region of the dispenser (2).

15. The dispensing device (1) according to claim 14, wherein the excitation light (19) and the illuminating light (8) at least partially have a common beam path.

16. The dispensing device (1) according to claim 14, wherein
based on a further detection light (20), the imaging device (16) generates a further image of the region (6) and/or the at least one other region.

17. The dispensing device (1) according to claim 16, wherein
 a. the evaluation device (17) evaluates the detected further detection light (20) to determine a further optical property of the region (6) and/or of the at least one other region and/or
 b. based on the detected further detection light (20), the evaluation device (17) determines whether no fluorescent cell (3) and/or no fluorescent particle is arranged in the region (6) and/or the at least one other region or whether exactly one single fluorescent cell (3) and/or exactly one single fluorescent particle is arranged in the region (6) and/or another region and/or whether several cells (3) and/or several particles are arranged in the region.

18. The dispensing device (1) according to claim 14, wherein
the optical detection device (5) has a further imaging device (22) for generating a further image of the region (6) and/or the at least one other region based on a detected further detection light (20).

19. The dispensing device (1) according to claim 18, wherein the optical detection device (5) has a further evaluation device (23), wherein
 a. the further evaluation device (23) evaluates the detected further detection light (20) to determine a further optical property of the region (6) and/or of the at least one other region and/or wherein
 b. based on the further detection light (20), the further evaluation device (23) determines whether no fluorescent cell (3) and/or no fluorescent particle is arranged in the region (6) and/or the at least one other region or whether exactly one single fluorescent cell (3) and/or exactly one single fluorescent particle is arranged in the region (6) and/or another region and/or whether several cells (3) and/or several particles are arranged in the region.

20. The dispensing device (1) according to claim 1, further comprising a suction device for siphoning off the dispensed liquid.

21. The dispensing device (1) according to claim 1, wherein the deflection device (9) deflects the detection light (15) exactly twice to direct the detection light (15) from the region (6) of the dispenser (2) to the objective (12).

* * * * *